(12) United States Patent
Dahmani et al.

(10) Patent No.: US 9,791,515 B2
(45) Date of Patent: Oct. 17, 2017

(54) BATTERY PROTECTED AGAINST ELECTRIC ARCS

(71) Applicant: Commissariat à l'énergie atomique et aux énergies alternatives, Paris (FR)

(72) Inventors: Jawad Dahmani, Grenoble (FR); Viviane Cattin, Saint Egreve (FR); Pierre Perichon, Voiron (FR)

(73) Assignee: Commissariat à l'énergie atomique et aux énergies alternatives, Paris (FR)

( * ) Notice: Subject to any disclaimer, the term of this patent is extended or adjusted under 35 U.S.C. 154(b) by 47 days.

(21) Appl. No.: 14/390,928

(22) PCT Filed: Apr. 8, 2013

(86) PCT No.: PCT/EP2013/057269
§ 371 (c)(1),
(2) Date: Oct. 6, 2014

(87) PCT Pub. No.: WO2013/150157
PCT Pub. Date: Oct. 10, 2013

(65) Prior Publication Data
US 2015/0061696 A1    Mar. 5, 2015

(30) Foreign Application Priority Data

Apr. 6, 2012    (FR) .................................... 12 53203

(51) Int. Cl.
*G01R 31/36*    (2006.01)
*G01N 29/28*    (2006.01)
(Continued)

(52) U.S. Cl.
CPC ......... *G01R 31/3627* (2013.01); *G01N 29/09* (2013.01); *G01N 29/14* (2013.01);
(Continued)

(58) Field of Classification Search
CPC ............ G01R 31/3627; G01R 31/1209; G01R 31/1227; G01R 31/3606; G01R 31/3648;
(Continued)

(56) References Cited

U.S. PATENT DOCUMENTS 4,442,700 A * 4/1984 Swoboda ................ G01N 9/24
73/32 A
7,411,403 B2 * 8/2008 Zhou ..................... G01R 31/026
324/500
(Continued)

FOREIGN PATENT DOCUMENTS

FR    2827675 A1 *  1/2003  ........... G01R 31/024
JP    2010-101706       5/2010

OTHER PUBLICATIONS

Knowles Acoustics, "Ultrasonic MEMS Sensor SPM0404UD5", Pub. Date: May 6, 2011, Date Viewed: Feb. 2, 2016, Published by: Digi-Key Electronics, http://www.digikey.com/en/articles/techzone/2011/may/ultrasonic-mems-sensor-spm0404ud5, pp. 1-4.*

(Continued)

*Primary Examiner* — Melissa Koval
*Assistant Examiner* — Rahul Maini
(74) *Attorney, Agent, or Firm* — Occhiuti & Rohlicek LLP

(57) ABSTRACT

The invention relates to a DC electrical power supply source including
a protective housing and
electrical energy storage devices disposed in the protective housing.
The storage devices are connected electrically in series by way of interconnection elements. There is
an acoustic sensor configured to measure ultrasounds and
a filling medium disposed in the housing.

(Continued)

The filling medium exhibits a homogeneous acoustic impedance and forms a continuous acoustic link between the interconnection elements and the acoustic sensor.

12 Claims, 3 Drawing Sheets

(51) Int. Cl.
| | |
|---|---|
| *G01N 29/09* | (2006.01) |
| *H01M 10/48* | (2006.01) |
| *G01R 31/12* | (2006.01) |
| *G01N 29/14* | (2006.01) |
| *H01M 10/0525* | (2010.01) |
| *H01M 10/42* | (2006.01) |

(52) U.S. Cl.
CPC ......... *G01N 29/28* (2013.01); *G01R 31/1209* (2013.01); *G01R 31/1227* (2013.01); *G01R 31/3606* (2013.01); *G01R 31/3648* (2013.01); *H01M 10/482* (2013.01); *G01N 2291/2697* (2013.01); *H01M 10/0525* (2013.01); *H01M 10/425* (2013.01)

(58) Field of Classification Search
CPC ........ G01N 29/09; G01N 29/14; G01N 29/28; G01N 2291/2697; H01M 10/482; H01M 10/0525; Y02T 10/7011

USPC ......................................................... 324/551
See application file for complete search history.

(56) References Cited

U.S. PATENT DOCUMENTS

| | | | |
|---|---|---|---|
| 8,279,074 B2* | 10/2012 | Fischer .............. | G01R 31/3658 320/130 |
| 8,754,660 B2* | 6/2014 | Kandori ................ | B06B 1/0292 324/661 |
| 2006/0209632 A1* | 9/2006 | Goodman .............. | G01N 29/14 367/13 |
| 2011/0267721 A1 | 11/2011 | Chaintreuil et al. | |

OTHER PUBLICATIONS

Cadoux, Yvan, Dispositif et Procede de Survellance de Reseau Electrique et Installation Comportant un Tel Dispositif, FR 2827675 A1 Translation, Pub Date: Jan. 24, 2003, Assignee: Schneider Electric Industries SA.*

Joseph Luis, "Detection of Electric Arcs in 42-volts Automotive Systems," pp. 1-139 (2003).

* cited by examiner

BATTERY PROTECTED AGAINST ELECTRIC ARCS

RELATED APPLICATIONS

This application is a U.S. National Stage of international application number PCT/EP2013/057269 filed Apr. 8, 2012, which claims the benefit of the priority date of French Patent Application FR 1253203, filed Apr. 6, 2012, the contents of which are herein incorporated by reference.

FIELD OF INVENTION

The invention relates to the storage of electrical energy, for example in electrochemical accumulator batteries. The latter may, for example, be used in the field of electric and hybrid transports or onboard systems. Such batteries may also be used as backup power supplies.

BACKGROUND

Hybrid combustion/electric or electric vehicles include, in particular, high-power batteries. Such batteries are used to drive an AC electric motor by way of an inverter. The voltage levels required for such motors reach several hundred Volts, typically of the order of 400 Volts. Such batteries also comprise a high capacity so as to further the vehicle's range in electric mode.

To obtain high powers and capacities, several groups of accumulators are placed in series. To facilitate the manufacture and the handling of the battery, the accumulators are generally grouped together in several modules connected in series. The number of stages in a module and the number of accumulators in parallel in each stage vary as a function of the desired voltage, current and capacity of the battery. The electrochemical accumulators used for such vehicles are generally of the ion lithium type for their capacity to store significant energy with a contained weight and volume. Battery technologies of Lithium ion iron phosphate LiFePO4 type form the subject of significant developments on account of a high intrinsic level of safety, to the detriment of a somewhat restricted energy storage density. An electrochemical accumulator customarily has a nominal voltage of the following order of magnitude:

3.3 V for a lithium-ion iron phosphate technology, LiFePO4, 4.2 V for a technology of cobalt oxide based lithium-ion type.

The document "Detection of Electric Arcs in 42-Volt Automotive Systems" describes various methods for detecting arcs. This document describes in particular a method for detecting arcs by ultrasound. In practice, this document describes the fact that acoustic sensors have to be distributed at various places in the vehicle to detect arcs for various localities of the electrical harness. Acoustic sensors are also envisaged for detecting arcs for interconnections of an electrical source, the source and the interconnections being protected in a housing, therefore forming a separation with the exterior. This document concludes as to the impossibility at this juncture of obtaining a locating solution based solely on acoustic sensors, on account of sensitivity to errors. This document does not afford any solution to the detection of electric arcs of the interconnections of the electrical source.

Document U.S. Pat. No. 4,442,700 describes a device for measuring the humidity inside a battery. This document describes in particular a battery furnished with a protective housing and electrical energy storage cells disposed in the housing and connected electrically in series by interconnection elements. Bus bars serve to connect plates of one and the same cell. Liquid electrolyte bathes the plates inside the housing. Acoustic sensors are disposed against the wall outside the housing and are thus protected against the corrosion of the electrolyte. On the basis of the measurement of the sensors, the document proposes to determine the humidity and the state of charge of the battery.

Document JP2010-101706 describes a battery accommodated in a protective housing. The battery is furnished with an ultrasound transducer fixed outside the battery and used to emit an ultrasound signal in the battery and to measure the ultrasound response of the battery. As a function of the response, a circuit determines the capacity of this battery. This determination of capacity is based on the diffusion of compounds in the electrolyte with battery wear, which modifies the ultrasound response.

Given the quantities of energy stored in power batteries intended for the traction of automotive vehicles, failures of such batteries may have considerable consequences.

One type of potential failure is the occurrence of electric arcs at the level of the series connection between electrochemical accumulators. Electric arcs usually result from wear, corrosion, vibrations, or an accident related impact. With a DC voltage source, such as a battery, the electric arcs remain struck as long as current is drawn by an electric load.

Electric arcs appear when a space is created between two electrical conductors in which current flows and electrical conduction continues across this space. The arc comprises two arc foot zones extending from the two respective electrical conductors. These arc foot zones generally exhibit a length of between 5 and 10 µm and a temperature of the order of the melting temperature of the two electrical conductors. This temperature is, for example, on the order of 1000° C. for copper electrical conductors. These arc foot zones are separated by a plasma exhibiting a temperature of the order of 10,000° C. for example. This temperature depends on the thermal equilibrium between the energy intake related to the current and the cooling by radiation essentially. The more significant the current and/or the shorter the arc, the higher is this temperature.

Electric arcs induce extremely high heating that may result in the melting of a connecting joint between the accumulators and surrounding materials.

Thus, if such electric arcs are not detected sufficiently early, their consequence may be the starting of a fire. Consequently, a need exists to detect occurrence of electric arcs. The detection of an electric arc turns out to be relatively arduous in a battery, the electrochemical cells generally being accommodated permanently in protective housings. The battery exhibits a complex structure with numerous mechanically isolated zones that are difficult to access. Moreover, a battery comprises a large number of interconnections that are liable to generate an electric arc.

A generic procedure for detecting arcs is based on a measurement of current and voltage. The occurrence of an electric arc induces disturbances in the voltage and the current at the terminals of the battery. By appropriate signal processing of these measurements, it is possible to detect the occurrence of an electric arc in certain applications. This solution is, however, inapplicable for batteries, since the electrochemical accumulators exhibit a very low impedance that attenuates the voltage signature of electric arcs. To alleviate this problem of detection, a large number of sensors ought to be used. This would induce an inappropriate cost for the detector.

Another generic procedure for detecting arcs relies on the measurement of optical radiation. In the presence of an electric arc, a very particular optical radiation is emitted. This radiation comprises the superposition of a continuous spectrum and of a discontinuous spectrum. The continuous spectrum is emitted during collisions of the electrons with the ions or atoms of the plasma. The discontinuous spectrum corresponds to photons, of well-determined frequencies, emitted by an atom, an ion, or a molecule that passes from one energy level to a lower energy level. This solution is, however, inapplicable for batteries, since the radiation sensor would be incapable of detecting the radiation of certain connections occluded by a protective housing of complex shape or disposed in the core of a module and occluded by electrochemical accumulators.

Another procedure for detecting arcs is used in photovoltaic panels. This procedure is based on the measurement of the electromagnetic field and the identification of a specific signature. Such detection induces a significant number of false alarms especially when the surrounding electromagnetic noise is significant. Such a solution is therefore unsuitable for automobile applications, subject to significant spurious glitches in the radiofrequency domain, in particular on account of the electric motorization. Moreover, such detection is greatly affected by any screen to the propagation of electromagnetic waves, the metallic elements such as a battery case or the chassis of the vehicle forming such screens. Furthermore, such detection exhibits a relatively long response time.

Another procedure for detecting electric arcs is used for overhead electric lines. Accordingly, use is made of a detector furnished with an acoustic sensor exhibiting a resonant frequency of 40 kHz. An electric arc indeed generally appears through the emission of an acoustic wave whose spectrum includes such a frequency. The acoustic sensor therefore measures a very specific value of the ultrasound disturbances in proximity to electric lines. The acoustic sensor exhibits very strong directivity. The signal provided by the acoustic sensor is modulated toward frequencies of the audible spectrum. The audible signal is provided to an operator by way of earphones. The operator determines the presence of electric arcs through the occurrence of an audible sound in the earphones. Such a detector is not applicable to a battery since the electrochemical accumulators are separated from the operator by the protective housing.

Thus, no procedure for detecting electric arcs in a power electrochemical accumulator battery is satisfactory for industrial application.

SUMMARY OF INVENTION

The invention is aimed at solving one or more of these drawbacks. The invention thus pertains to a DC electrical power supply source, such as detailed in the appended claims.

Other characteristics and advantages of the invention will emerge clearly from the description thereof given hereinafter, by way of wholly nonlimiting indication, with reference to the appended drawings.

DETAILED DESCRIPTION

The invention proposes to detect the occurrence of electric arcs in a DC electrical power supply source comprising a plurality of electrical energy storage devices connected electrically in series by way of interconnection elements. These storage devices are accommodated in a housing in which there is a filling medium having a homogeneous acoustic impedance. This filling medium forms a continuous acoustic link between these interconnection elements and an ultrasound acoustic sensor.

An ultrasound measurement inside the housing makes it possible at one and the same time to detect the occurrence of arcs at various localities, even masked, inside the housing, and to ensure much reduced sensitivity to sources of exterior disturbances, the housing ensuring very effective filtration with respect to possible exterior electric arcs on account of the change of medium that it induces.

The detection of the ultrasound vibrations propagated by the filling medium is favored with respect to a solution with propagation through the electrical connection or through the structural elements, the series electrical connection in the battery 1 comprising a large number of discontinuities and such propagation turning out to be sensitive to disturbances arising from the exterior.

For example, in an automotive vehicle, a very large number of components may generate electric arcs during their normal operation (for example the blinkers) and the latter must therefore be discriminated from an electric arc occurring in the power supply battery or an electrical traction motor power.

Figure 1:
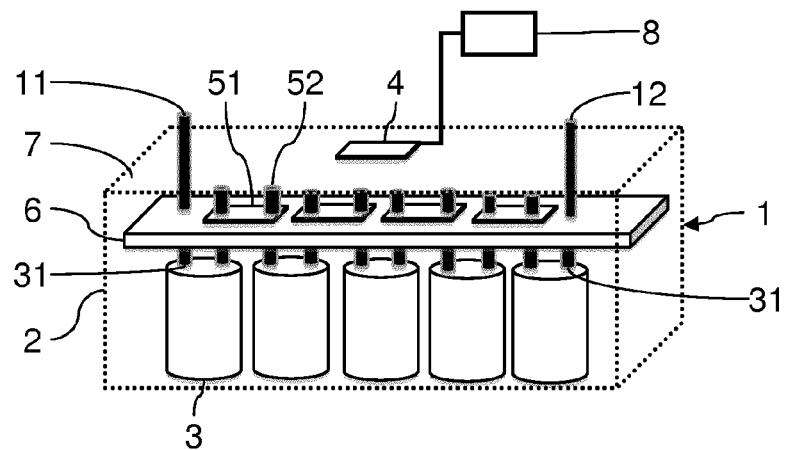
FIG. 1 is a perspective schematic representation of a first exemplary implementation of electric arc detection according to the invention.

FIG. 1 is a perspective schematic representation of a first exemplary implementation of the detection of an electric arc in a battery 1. The battery 1 comprises a protective housing 2. Electrical energy storage devices 3 in the form of electrochemical accumulators are accommodated inside the housing 2. The protective housing 2 protects in particular in a manner known per se the electrochemical accumulators 3 from dust, protects persons from electrical contacts and protects the exterior environment from the consequences of the possible destruction of one of these accumulators. The electrochemical accumulators 3 illustrated are connected electrically in series between two terminals 11 and 12 of the battery 1. The battery 1 is typically a power battery able to apply a voltage at least equal to 25V, generally at least equal to 50 V, and more frequently at least equal to 100V across its terminals.

Each electrochemical accumulator 3 comprises two terminals 31 of opposite polarities. The series connection between the terminals 31 of the various accumulators 3 is effected here by way of interconnection elements 51, typically in the form of metallic blades. These interconnection elements 51 are maintained in electrical contact with the terminals 31 by way of screws 52 screwed into the terminals 31. It is also possible to envisage electrical contact between the interconnection elements 51 and the terminals 31 that is effected by means of welds or sprung elastic connections. The series link between two accumulators 3 exhibits a discontinuity of matter on account of the use of these interconnections 51. The interconnection elements 51 can be disposed on a substrate 6. The substrate 6 can comprise various electronic circuits, for example for measuring the voltage across the terminals of the electrochemical accumulators or for measuring the temperature inside the housing 2.

An electric arc originates in the filling medium 7 in which the interconnection elements 51 are sunk. Because of its homogeneous acoustic impedance and the continuous acoustic link that it forms between the sensor 4 and the interconnection element confronted with an electric arc, the filling medium 7 propagates the ultrasound waves to this sensor 4.

The filling medium 7 is an electrical insulant. The filling medium 7 advantageously comprises a very different acoustic impedance from the acoustic impedance of the walls of the protective housing 2. On account of this difference in impedance, when an ultrasound acoustic wave generated by an electric arc propagates in the filling medium 7 and encounters a wall of the housing 2, the acoustic energy is essentially reflected by the wall and continues to propagate in the filling medium 7. Likewise, the acoustic wave is essentially reflected when it encounters other components in the housing 2. The echoes of the generated wave thus exhibit a sufficiently high amplitude to be detected by a sensor 4. Consequently, the ultrasound vibration generated by an electric arc propagates a significant distance inside the housing 2 and up to the sensor 4, thereby making it possible to detect electric arcs even for interconnections that are isolated or masked by other components. The proportion of the acoustic energy absorbed by the wall of the housing 2 and transmitted through the wall of the housing 2 is thus reduced. Furthermore, the ultrasound acoustic disturbances outside the housing 2 are transmitted to the filling medium 7, but only with a very large attenuation. The precision of the detection of an electric arc inside the housing 2 is thus optimized.

The filling medium 7 can typically be air, an inert gas or a phase change material such as an organic phase change material. A phase change material is typically used to reduce the speed of propagation of warming in the battery 1, when a sharp increase in temperature localized inside the housing 2 appears.

Usually, even for a battery 1 furnished with a liquid cooling circuit for its electrochemical accumulators, the terminals of the accumulators and the interconnection elements are placed in air, the air ensuring a continuous link between these various interconnection elements. Such a configuration is usually adopted for reasons of assembly of the electrochemical accumulators of the battery 3.

The protective housing 2 is typically made of synthetic materials, for example polymer materials, but may also be made of metal (molded aluminum for example). The protective housing 2 is advantageously leak-tight, so as to isolate the sensor 4 from exterior acoustic disturbances.

The acoustic sensor 4 is advantageously configured to measure ultrasounds with a bandwidth extending between 20 kHz and 150 kHz. Numerous industrial ultrasound sensors exhibit a detection spike at about 40 kHz. At 40 kHz, the ultrasound wave is little attenuated in the air and remains fairly directional. To make it possible to detect the occurrence of electric arcs at numerous different localities, the acoustic sensor 4 advantageously comprises a main reception lobe exhibiting an aperture of at least equal to 90°, preferably at least equal to 100°, and preferentially at least equal to 120°. The sensor marketed under the commercial reference R15-alpha by the company EPA has in particular turned out to be satisfactory in tests carried out.

In particular, when the filling medium 7 is air or a gas, the acoustic sensor 4 is advantageously chosen from the group comprising membrane-based sensors, sensors of MEMS type, and capacitive sensors.

Here, the acoustic sensor 4 is fixed inside the housing 2 against a wall of this housing. The part of the sensor 4 performing the measurement of the ultrasound wave is in contact with the filling medium 7 and advantageously spaced from the housing 2. The housing 2 is advantageously acoustically leak-tight. A discontinuity of propagation medium is formed by the housing 2 between the exterior and the interior of this housing. It is possible, however, to envisage placing this sensor 4 in any appropriate place, for example on the substrate 6.

An electronic processing circuit 8 is connected to the acoustic sensor 4 to ensure the detection of the occurrence of an electric arc. Procedures for electric arc detection as a function of the response of the acoustic sensor 4 will be detailed subsequently.

Figure 2:
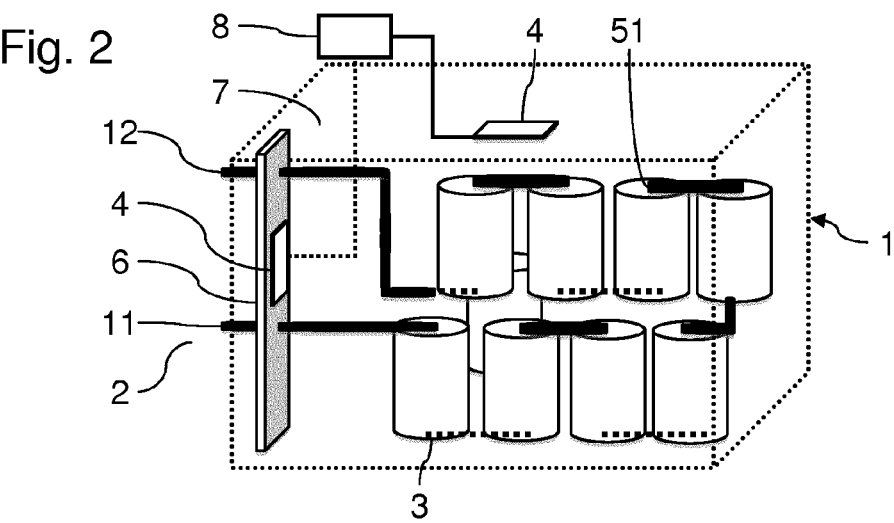
FIG. 2 is a perspective schematic representation of a second exemplary implementation of electric arc detection according to the invention.

FIG. 2 is a perspective schematic representation of a second exemplary implementation of the detection of an electric arc in a battery 1. The housing 2 and the filling medium 7 are substantially identical to those mentioned with reference to FIG. 1. In this example, the electrochemical accumulators 3 are connected electrically in series between two terminals 11 and 12 of the battery 1. The accumulators 3 are connected in series by way of interconnection elements 51. The ends of an interconnection element 51 are welded onto respective terminals of two accumulators 3.

Several ultrasound sensors are disposed inside the housing 2. The various ultrasound sensors 4 are distributed in an appropriate manner inside the housing 2. Certain ultrasound sensors may be fixed on the walls of the housing 2, other sensors may be disposed against walls of the housing 2. The sensors 4 are acoustically linked with the interconnection elements 51.

The interconnections between one and the same branch of series-connected accumulators 3 have been illustrated in FIG. 2. The battery 1 can of course comprise other branches connected electrically in parallel with the branch illustrated.

By using a plurality of sensors 4, it is advantageously possible to determine a position of the electric arc generated. The electronic processing circuit 8 can for example compare the responses provided by various sensors 4. As a function of the amplitude and of the temporal shift between these responses (for example the temporal shift between the measurement spikes measured by the various sensors 4), it is possible to determine the distance separating the various sensors 4 from the electric arc. A triangulation technique makes it possible in particular to locate the site of the electric arc.

The use of a plurality of sensors 4 also makes it possible to improve the reliability of the detection of an arc in a heavily congested environment inside the housing 2.

Figure 3:
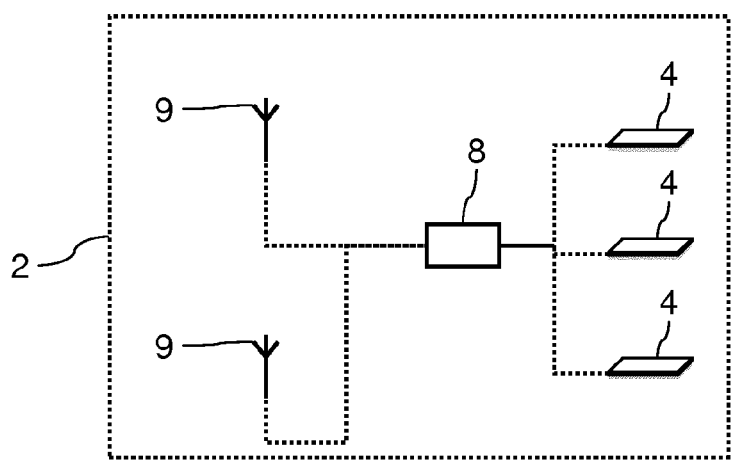
FIG. 3 is a schematic representation of a detection module according to a variant of the invention.

FIG. 3 illustrates an example of a battery 1 comprising an enhancement for the detection of electric arcs. The battery 1 includes at least one electromagnetic sensor 9. The battery 1 illustrated here includes two electromagnetic sensors 9 disposed at various localities inside the housing 2. The electromagnetic sensors 9 are connected to the electronic processing circuit 8.

On account of the enormous difference in propagation speed between the electromagnetic wave and the vibratory wave that are generated by the occurrence of an electric arc, the processing circuit 8 is able to determine the instant of occurrence of the electric arc on the basis of the signal measured by a sensor 9 and can thereafter determine the distance between the electric arc and a sensor 4 on the basis of the temporal shift between the detection of the arc by this sensor 4 and the detection by a sensor 9. On account of the greater reliability of the measurements performed by the ultrasound sensor 4, the circuit 8 advantageously determines the occurrence of an electric arc on the basis of the measurements of the ultrasound sensors 4 and uses the measurements of the electromagnetic sensors 9 solely to optimize location of the electric arc.

The combination of detection by an electromagnetic sensor and by an ultrasound sensor furthermore makes it possible to reduce the probability of detection of a false alarm.

The electromagnetic sensor can also make it possible to trigger the acquisition of ultrasound vibrations.

The vibratory signature of an electric arc is a very broadband ultrasound transient signal. This vibratory wave is omnidirectional, thereby facilitating the detection of the electric arc even if isolated or masked by other components.

The vibratory wave propagates while undergoing phenomena of reflection, refraction, diffusion, and absorption. These contribute to the progressive attenuation of the wave, which is manifested by a decaying of the amplitude of the sound oscillations with distance. The global attenuation of the ultrasound vibration is exponential and corresponds globally to the relation hereinbelow:

$$I = I_0 * e^{-\alpha x}$$

The intensity, denoted I, is defined as the power of the ultrasound wave per unit area, with α the attenuation coefficient and x the thickness traversed.

The wave undergoes absorption: part of the ultrasound energy is transformed into heat. This phenomenon causes heating of the medium in which the wave propagates. Diffusion takes place if the ultrasounds encounter an object or an aperture of smaller dimension or of the order of their wavelength. The diffusion is manifested by the propagation of the beam in a direction other than the direction of incidence. When an ultrasound wave encounters, at normal incidence, an interface between two media of different acoustic impedances, it undergoes a reflection and a transmission whose power ratio is dependent on the impedances of the two media according to the relation hereinbelow:

$$R = \frac{E_{ref}}{E_{incid}} = \left(\frac{Z_1 - Z_2}{Z_1 + Z_2}\right)^2$$

Figure 4:
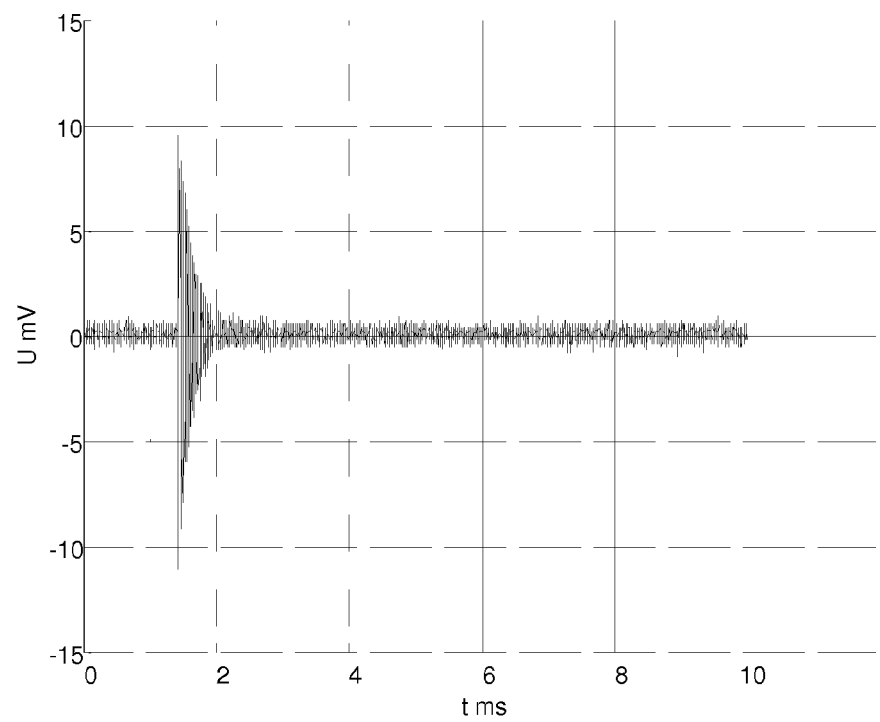
FIG. 4 is a graph illustrating an exemplary temporal response generated by an ultrasound sensor subsequent to the occurrence of an electric arc.
Figure 5:
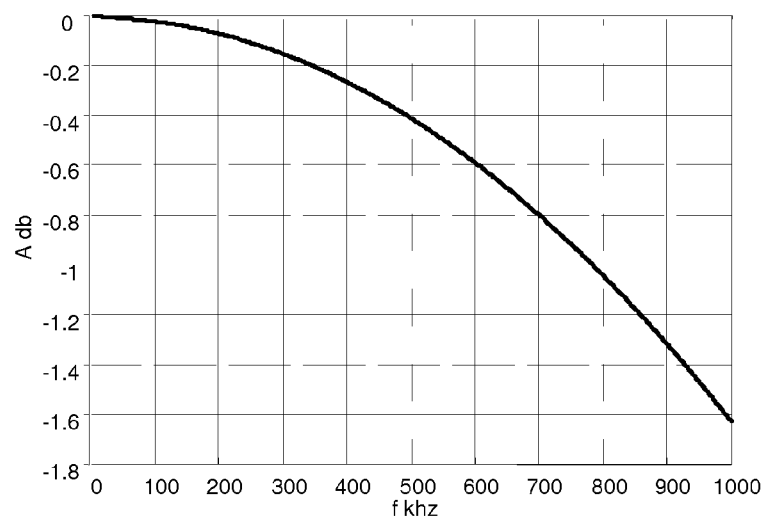
FIG. 5 is a graph of the response in terms of acoustic frequency of the air.

Calculations undertaken at the air/accumulator interface show that almost all of the ultrasound wave is reflected (99.9%) with the parameters hereinbelow:

the impedance of the air $Z^{air} = \rho^{air} * c^{air} = 440$ kg.m$^{-2}$.s$^{-1}$ the impedance of an accumulator $Z^{ele} = \rho^{ele} * c^{ele} = 4.5*10^6$ kg.m$^{-2}$.s$^{-1}$ FIG. 4 illustrates an exemplary temporal response in terms of voltage of an ultrasound sensor 4 subsequent to the occurrence of an electric arc. The instant 0 corresponds to the occurrence of the electric arc. The sensor 4 being remote from the electric arc generated, the sensor 4 does not immediately detect the ultrasound vibration induced by the electric arc. The sensor 4 then measures a background noise. When the ultrasound wave propagating in the filling medium 7 reaches the sensor 4, the latter measures an acoustic wave spike followed by a set of damped oscillations, with an exponential decay.

Various procedures for detecting electric arcs are possible on the basis of the responses measured by the ultrasound sensors.

As the electric arcs may induce various shapes of ultrasound response, provision may be made to store beforehand various response profiles of the sensors 4 corresponding to electric arcs. The stored response profiles can then be compared with the responses measured by the sensors 4.

Various models of electric arcs can be stored, with various amplitudes and/or various rates of decay.

The ultrasound signature of an electric arc can be modeled by an autoregressive filter of ARMA type. Other procedures such as those consisting in using a matched filter or a neural net can also be used.

For the modeling of an electric arc by an ARMA regressive filter, a database of measurements of ultrasound sensors corresponding to various types of electric arcs is used. For each of these arcs, the order of the ARMA filter whose impulse response best approximates the corresponding measured signal is determined. To assess the matching of the ARMA filter modeling the arc, the mean square error of the model is evaluated with respect to the measured signal.

When the sensor 4 provides a measurement to the circuit 8, the latter calculates for example an inter correlation of the measured signal with the various stored models of ARMA filter type. Accordingly, a sliding window is applied to the measured signal and a normalized coefficient of correlation between the model and the signal measured for each window is calculated. The calculation of a normalized correlation coefficient coeff can be as follows:

$$\text{coeff} = \frac{\text{corr}(stest, smod)}{\|stest\|_2 \cdot \|smod\|_2}$$

with stest being the signal measured for a window and smod the signal of the model.

If the value of the coefficient coeff exceeds a predetermined threshold (corresponding to a threshold of sensitivity to a false alarm), the circuit 8 determines the presence of an electric arc.

Tests have been carried out on the basis of such a calculation of correlation between an ARMA model and a measured signal. These tests have made it possible to determine that even with mediocre isolation with respect to various ultrasound sources, the use of correlation with arc models was very discriminating and greatly limited the risks of false alarm. On account of the good prior knowledge of the profile of the ultrasound vibration, the use of correlation gives excellent results to eliminate detections of false alarms. Moreover, such detection based on correlation is quite insensitive to the superposition of a signal transmitted directly to the sensor 4 by the filling medium 7 with echoes arriving at the sensor 4.

Figure 6:
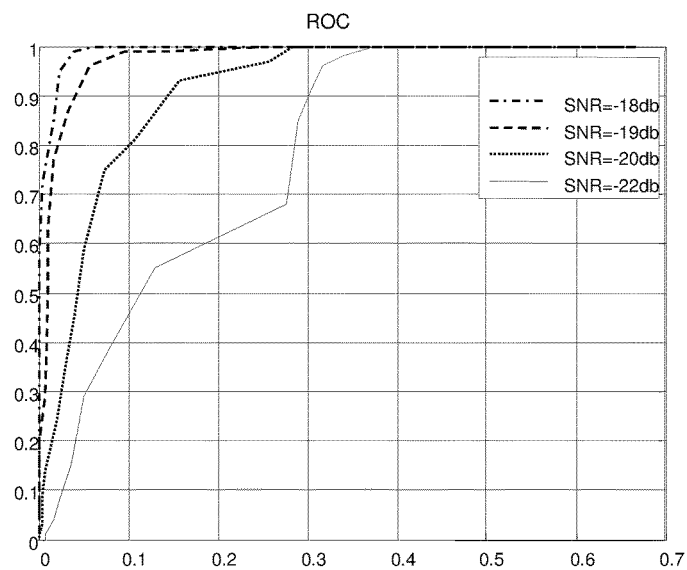
FIG. 6 illustrates graphs of receiver operational characteristic ("ROC") obtained for the arc detection according to an example of the invention, for various levels of noise.

The reliability of detection is in particular illustrated by the ROC curves of FIG. 6, simulated as a function of various noise levels (probability of false detection along the abscissa, probability of detection along the ordinate).

Optionally, other noise sources exhibiting similar signatures (an automotive vehicle blinker generates periodic electric arcs) could be discriminated in the event of poor isolation of the interior of the battery, by identifying for example distinctive characteristics of the source of disturbances. A blinker is, for example, identifiable on account of the periodicity of the electric arcs that it generates or on account of a lower amplitude of the vibrations.

To improve the reliability of arc detection, it is possible to carry out a programmed modulation of the electric load connected to the battery. Such a modulation being manifested by a modulation on the possible acoustic emission of the arc (a physical phenomenon known as singing arc), an analysis of correlation between the modulation of the current drawn from the battery and the measured modulation on the acoustic vibration is possible. The modulation of current can be defined by a circuit for supervising the battery 1, this supervising circuit communicating with the electronic processing circuit 8 to provide it with parameters of the current modulation applied.

A battery can be organized as a plurality of modules interconnected electrically in series and/or in parallel, each module including a plurality of electrically interconnected electrochemical accumulators. By individualizing the detection of an electric arc for each module, provision may be made to isolate a failed module so as to ensure continuity of service of the battery. For this purpose, each module can be furnished with a failsafe device such as described in patent application FR1155349. The other modules connected in series with the failed module can thus continue to supply the terminals of the battery.

Although the invention has been described with reference to an electrochemical accumulator battery, the invention also applies to other DC electrical power supply sources including multiple energy storage devices connected in series by way of interconnection elements.

The invention claimed is:

1. A DC electrical power supply source, comprising:
a protective housing;
electrical energy storage devices disposed in the protective housing, said storage devices being connected electrically in series by way of interconnection elements;
an acoustic sensor disposed in the protective housing, said acoustic sensor configured to measure ultrasounds; and
a filling medium disposed in the protective housing;
wherein the filling medium exhibits a homogeneous acoustic impedance and forms a continuous acoustic link between said interconnection elements and the acoustic sensor; and
wherein the protective housing is leaktight so as to isolate the acoustic sensor from exterior acoustic disturbances.

2. The DC electrical power supply source as claimed in claim 1, further comprising an electronic circuit configured to detect the occurrence of an electric arc as a function of the ultrasounds measured by the acoustic sensor.

3. The DC electrical power supply source, as claimed in claim 2, comprising a plurality of acoustic sensors distributed within the protective housing and configured to measure ultrasounds, the filling medium forming a continuous acoustic link between the interconnection elements and the plurality of acoustic sensors, and the electronic circuit being configured to determine the position of the electric arc as a function of the respective measurements of an ultrasound spike by each of said plurality of acoustic sensors.

4. The DC electrical power supply source as claimed in claim 2, further comprising an electromagnetic sensor disposed in the protective housing, the electronic circuit being configured to confirm a detection of occurrence of an electric arc as a function of the electromagnetic signal measured by the electromagnetic sensor.

5. The DC electrical power supply source as claimed in claim 4, in which the electronic circuit is configured to determine the position of the electric arc as a function of a duration between an ultrasound spike measured by the ultrasound sensor and an electromagnetic spike measured by the electromagnetic sensor.

6. The DC power supply source as claimed in claim 2, in which the electronic circuit is configured to calculate coefficient between the ultrasounds measured and a model of vibration generated by an electric arc, the electronic circuit being configured to detect the occurrence of an electric arc when the calculated coefficient exceeds a threshold.

7. The DC electrical power supply source as claimed in claim 2, in which the electronic circuit is configured to:
control a predefined modulation of an electric load connected to the power supply source;
calculate cross-correlation between the measured ultrasounds and the controlled electric load modulation; and
detect the occurrence of an electric arc as a function of the calculated cross-correlation.

8. The DC electrical power supply source as claimed in claim 1, in which the acoustic sensor is configured to measure ultrasounds with a bandwidth extending at least between 20 kHz and 150 kHz.

9. The DC electrical power supply source as claimed in claim 1, in which the acoustic sensor is chosen from the group comprising membrane-based sensors, sensors of MEMS type and capacitive sensors.

10. The DC electrical power supply source as claimed in claim 1, in which the acoustic sensor comprises a main reception lobe exhibiting an aperture of at least equal to 90°.

11. The DC electrical power supply source as claimed in claim 1, in which the filling medium is air.

12. The DC electrical power supply source as claimed in claim 1, in which a part of the acoustic sensor performing an ultrasound wave measurement is in contact with the filling medium.

* * * * *